United States Patent [19]

Gennari

[11] Patent Number: 5,102,791

[45] Date of Patent: * Apr. 7, 1992

[54] STABLE SULPHO-ADENDOYL-L-METHIONINE (SAME) SALTS, PARTICLARLY SUITABLE FOR PARENTERAL USE

[75] Inventor: Fedrico Gennari, Truccazzano, Italy

[73] Assignee: Bioresearch S.p.a., Milan, Italy

[*] Notice: The portion of the term of this patent subsequent to Nov. 4, 2003 has been disclaimed.

[21] Appl. No.: 732,287

[22] Filed: May 9, 1985

[30] Foreign Application Priority Data

May 16, 1984 [IT] Italy ................. 20938 A/84

[51] Int. Cl.$^5$ ................. C12P 13/12; C12N 1/18; C07H 19/06
[52] U.S. Cl. ................. 435/113; 435/256; 536/26
[58] Field of Search ............ 435/88, 113, 84, 85, 435/87, 255, 256; 536/26

[56] References Cited

U.S. PATENT DOCUMENTS

| | | | |
|---|---|---|---|
| 3,893,999 | 1/1975 | Fiecchi | 536/26 |
| 3,954,726 | 5/1976 | Fiecchi | 435/119 |
| 4,057,686 | 11/1977 | Fiecchi | 536/26 |
| 4,562,149 | 12/1985 | Shiocaki et al. | 435/88 |
| 4,621,056 | 11/1986 | Gennari | 435/85 |

FOREIGN PATENT DOCUMENTS

| | | | |
|---|---|---|---|
| 0107485 | 9/1978 | Japan | 536/26 |
| 2064532 | 6/1981 | United Kingdom . | |

OTHER PUBLICATIONS

*Kirk-Othmer Encyclopedia of Chemical Technology*, 2nd. ed., vol. 22, p. 541 (1970).
*The Yeasts*, Elseiver Science publishers B. V., Amsterdam, pp. 39–42 and 822 (1984).

*Primary Examiner*—Elizabeth C. Weimar
*Attorney, Agent, or Firm*—Stevens, Davis, Miller & Mosher

[57] ABSTRACT

The present invention relates to new stable sulpho-adenosyl-L-methionine (SAMe) salts particulary suitable for parenteral use, their production process, and pharmaceutical compositions containing them as active principles.

Said salts correspond to the general formula:

$$SAMe.n(CH_2)_m(SO_3H)_2 \qquad (I)$$

where n can vary from 1 to 2 and m can vary from 3 to 12.

The process for producing said salts consists of the following stages: a) enriching the starting yeast with SAMe; b) lysing the cells and recovering a solution rich in SAMe (cell lysate); c) prepurifying the cell lysate by ultrafiltration; d) passing the prepurified lysate through a column of weak acid ion exchange resin and eluting with the required disulphonic acid; e) passing the eluate of said column through a colum of absorption resin and washing with the required disulphonic acid; f) concentrating the eluate of the later column by reverse osmosis; g) drying the concentrated solution.

13 Claims, No Drawings

STABLE SULPHO-ADENDOYL-L-METHIONINE (SAME) SALTS, PARTICLARLY SUITABLE FOR PARENTERAL USE

This invention relates to new stable sulpho-adenosyl-L-methionine (SAMe) salts.

More particularly, the invention relates to salts deriving from the reaction between SAMe and disulphonic acids, their production process, and pharmaceutical compositions which contain them as active principles.

Said salts are particularly suitable for parenteral use.

SAMe is the main biological donor of methyl groups, and because of this characteristic it is of considerable interest both from the biological viewpoint and from the point of view of its therapeutic applications.

However, this product presents problems with regard to its large-scale use, these problems being connected with its thermal instability, even at ambient temperature, and with the complexity of its preparation and purification.

SAMe has therefore been the subject of numerous patents directed both towards the obtaining of new stable salts, and towards the provision of preparation processes which can be implemented on an industrial scale.

The present applicant has filed various patents relating both to new stable salts and to preparation methods for sulpho-adenosyl-L-methionine (Italian patents 1,043,885, 1,022,016, 1,022,036 and 1,054,175; Italian patent applications 23603A/81 and 22622A/83).

The salts discovered by the applicant as covered by the patents mentioned heretofore are all very stable and are suitable for pharmaceutical use.

They have however the drawback of very high acidity (high strong acid equivalents per equivalent of SAMe) because of which in their injectable forms the lyophylised vial containing the active principle has to be accompanied by a suitable buffer solvent which adjusts the pH of the final solution to within physiological values.

The high saline concentration of the buffer therefore prevents the use of high product doses.

The main advantage of the new salts according to the present invention is that they contain only 3 acid equivalents per equivalent of SAMe, and therefore require a considerably smaller buffer quantity for their neutralisation.

They are therefore particularly suitable for parenteral use of SAMe at high dosage, which has proved to be required in clinical use for certain affections.

Furthermore, the SAMe salts according to the present invention are indefinitely stable with time at a temperature up to 45° C., and are soluble in water up to a concentration of at least 30% by weight, and are insoluble in common organic solvents.

Finally, said salts can be easily prepared economically on an industrial scale by means of a high-yield process.

The sulpho-adenosyl-L-methionine (SAMe) salts according to the present invention are characterised by the general formula:

$$SAMe.n(CH_2)_m(SO_3H)_2 \qquad (I)$$

where n can vary from 1 to 2 and m can vary from 3 to 12.

The process for producing said salts, according to the present invention, is characterised by: a) enriching the starting yeast with SAMe; b) lysing the cells and recovering a solution rich in SAMe (cell lysate); c) prepurifying the cell lysate by ultrafiltration; d) passing the prepurified lysate through a column of weak acid ion exchange resin and eluting with the required sulphonic acid; e) passing the eluate of said column through a column of absorption resin and washing with the required sulphonic acid; f) concentrating the eluate of the latter column by means of reverse osmosis; g) drying the concentrated solution.

These and further characteristics and advantages of the SAMe salts according to the present invention will be more apparent from the detailed description given hereinafter which relates particularly to the production process and is described for illustrative purposes.

The stages of the process for producing SAMe salts according to the present invention are conducted in the following manner:

a) the starting yeast is enriched with SAMe by adding methionine to cultures of Saccharomyces Cerevisiae, Torulopsis utilis, Candida utilis etc., in the manner described by Schlenk [Enzymologia, 29, 238 (1965)];

b) cell lysis followed by recovery of a SAMe-rich aqueous solution (cell lysate): the lysis is effected by treating the enriched yeast firstly with a solution of water and ethyl acetate in a volume ratio of between 3:1 and 0.5:1 and preferably between 1.2:1 and 0.8:1; the quantity of the water-ethyl acetate solution used is preferably between 1/20 and ½, and preferably between ¼ and 1/5 of the moist cell weight, and the treatment is continued for a time of between 15 and 45 minutes, and preferably 30 minutes. Sulphuric acid of between 0.1N and 0.5N, and preferably 0.35N, is then added in a quantity of between 1:1 and 0.2:1 and preferably between 0.5:1 and 0.6:1 with respect to the moist cell weight. The treatment is continued for a time of between 1 and 2 hours and preferably 1.5 hours at ambient temperature. The cell lysis effected in this manner causes practically 100% of the SAMe present to pass into solution. It should be noted that lysing the yeast cells with a mixture of organic solvent and dilute sulphuric acid is considerably more convenient than with perchloric acid at ambient temperature or formic or acetic acid at 60° C. and the like, in that not only does the lysis take place at ambient temperature, which considerably favours SAMe stability, but is conducted under such conditions that the solution can be easily filtered from the cell residues, and contains none of the impurities which are present when the other lysing media are used, and which are difficult to remove by the known preparation processes for pure SAMe;

c) prepurification of the cell lysate by ultrafiltration: the cell lysate originating from stage b) is subjected to an ultrafiltration process using membranes with a 10,000 nominal cut-off, which enable the protein residues and high-molecular weight polysaccharide residues to be removed from the lysate and which would otherwise fix on to the ion exchange resins in the next stage, to progressively reduce their activity. The ultrafiltration process can be conducted either with flat membranes or, preferably, with tubular membranes. It should be noted that the use of ultrafiltration enables the resin columns of the next stage to be fed with a considerably more pure lysate, and in particular free from high molecular-weight substances which by irreversibly fixing on to the resins would progressively poison them, so reducing their activity and thus their purification capacity. This pretreatment therefore considerably increases the average life of the resins in the columns, which would otherwise have to be frequently replaced because of their poisoning, and thus reduces production costs;

d) passage of the prepurified lysate through a weak acid ion exchange resin: the permeate originating from stage c) is passed through a column of weak acid resin (COOH) in H+ form at a pH of between 3.5 and 7 and preferably pH 5, at a rate of between 1 and 3 liquid volumes/hour per resin volume, and preferably at a rate of 2 liquid volumes/hour per resin volume. The quantity of resin used is in the region of 10–50, and preferably 30, liters per kg of SAMe. The lysate is passed through the column, which is then washed with distilled water, and then with 0.1M acetic acid until the eluate has a pH of less than 3, and then with distilled water, and finally the SAMe is eluted with a 0.2N solution of the required disulphonic acid. The eluate containing the SAMe contains small quantities of coloured impurities and between 3% and 10% of 5'-deoxy-5'-methylthioadenosine (the main SAMe degradation product). These impurities are removed by using absorption resins (stage e);

e) passage of the eluate from the preceding column through an absorption column, and washing with the required sulphonic acid: it has been unexpectedly found that absorption polymers of polystyrene and acrylic ester such as thos identified by the tradenames Amberlite XAD2, Amberlite XAD4 or Amberlite XAD7 type, when in a strongly acid solution such as the eluate from the preceding column (stage d), retain practically no SAMe whereas they are able to easily adsorb coloured impurities, adenine and 5'-deoxy-5'-methylthioadenosine. Stage e) is effected by passing the eluate from stage d) through a column of one of the aforesaid resins, preferably Amberlite XAD4, at a rate of between 0.2 and 1 liquid volume/hour per resin volume, and preferably 0.5 liquid volumes/hour per resin volume. The resin quantity used is in the region of 10–50, preferably 30, liters/kg of SAMe. The SAMe solution is passed through the column, which is then washed with a 20 mN solution of the required disulphonic acid until SAMe disappears from the eluate. The eluate, containing about 10 g/l of very pure SAMe, is fed to the subsequent concentration stage f). It should be noted that the co-loured impurities are removed in the known art by using activated carbons, which although on the one hand are effective in removing this type of impurity, on the other hand irreversibly absorb a considerable quantity of SAMe (about 15% of the weight of the carbon used), thus leading to a considerable yield reduction. The advantage of absorption resins thus consists of the fact that the same degree of purification is obtained, but with a considerably higher yield than when using activated carbon;

f) concentration of the eluate of stage e) by means of reverse osmosis: stage f) is effected by subjecting the eluate from stage e) to a reverse osmosis process using desalination membranes of high NaCl rejection, which are able to practically completely retain the SAMe, while allowing water and part of the disulphonic acid to pass as permeate. Polyamide membranes are preferably used because of their high strength in strongly acid solution. Concentration by reverse osmosis enables the eluate from stage e) to be concentrated from 10 g/l to 100–150 g/l, and preferably to 120 g/l. The SAMe solution concentrated by reverse osmosis is analysed to determine the SAMe and disulphonic acid concentrations. A suitable quantity of disulphonic acid is added in order to obtain the required stoichiometric composition (preferably 3 acid equivalents per SAMe equivalent). This solution is fed to the subsequent drying stage g) which uses a spray dryer to obtain the final product;

g) drying of the concentrated solution: in this stage, the product is atomised in a drying chamber fed with hot air. The concentration of the inlet solution (expressed as SAMe) is between 100 and 200 g/l, and preferably 120 g/l. The feed temperature of the drying air, which has preferably been previously dehumidified, is between 140° and 200° C., and preferably 160° C. The outlet air temperature is preferably between 40° and 100° C., and preferably 60° C. Under these conditions, the outlet product has a temperature of between 40° and 60° C., and is cooled to ambient temperature by means of dehumidified air. Preferably, the plant operates with a suitable device for continuously extracting the dry product. It should be noted that the use of the spray dryer for the final product drying, compared with previously known methods such as lyophilisation, results in a considerable cost reduction and is more easily implemented on a large production scale.

The disulphonic SAMe salifying acids which are used for elution in the column comprising weak acid ion exchange resin (stage d) can be either obtained commercially or easily prepared in the form of disodium salts from the corresponding dibromides by reaction with sodium sulphite in accordance with the equation:

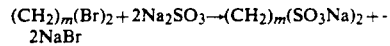

$$(CH_2)_m(Br)_2 + 2Na_2SO_3 \rightarrow (CH_2)_m(SO_3Na)_2 + 2NaBr$$

where m can vary from 3 to 13.

The reaction is conducted under reflux in a water-alcohol mixture containing preferably 7.5 parts of water, 2 parts of 95% ethanol and 0.5 parts of n-butanol, preferably for 3 days.

1 mole of alkyl dibromide as heretofore defined is suspended in 1 liter of water-alcohol mixture as heretofore defined, 2.2 moles of anhydrous sodium sulphite are added, and the mixture heated under reflux for 3 days.

On termination of the reaction the alcohols are removed by distillation, the aqueous solution is concentrated to a volume of between 0.5 and 1 liter, and the sulphonic acid disodium salt is allowed to crystallise under cold conditions (4° C.).

It is recrystallised from an equal volume of water, and the product is filtered off and dried under vacuum. The average yield of disodium salt is 90 mol %.

The disodium salt is redissolved in water of such a quantity as to obtain a 0.3N solution, and the solution obtained is fed through a column of strong acid ion exchange resin (Amberlite IR 120 or Dowex 50 type) in H+ form, which has been carefully activated and washed. The resin retains the sodium, and a solution of disulphonic acid is obtained at the column outlet.

The column is washed with distilled water to pH 4, the eluate is titrated and is diluted to obtain a 0.2N solution of disulphonic acid.

This solution is used in stages d) and e) of the SAMe production.

Non-limiting illustrative examples are given hereinafter of the process for producing the new stable SAMe salts of disulphonic acids according to the present invention, and of pharmaceutical compositions of said salts.

EXAMPLE 1

Preparation of 0.2N solutions of disulphonic acids of general formula $(CH_2)_m(SO_3H)_2$ 75 liters of distilled water, 20 liters of 95% ethanol and 5 liters of n-butanol are added to 21.6 kg (100 moles) of 1,4-dibromo butane. 26.46 kg (210 moles) of anhydrous sodium sulphite are added, and the mixture heated under reflux for 3 days.

On termination of the reaction, 20 liters of distilled water are added, and the mixture distilled until the alcohols are completely removed.

The mixture is diluted to a final volume of 60 liters with water and heated until complete dissolution has occurred.

The disodium salt of the 1,4-butanedisulphonic acid obtained is allowed to crystallise overnight at 4° C.

The product is filtered off and washed with 10 liters of water.

The mother liquors are concentrated under vacuum to a volume of 20 liters, and left to crystallise overnight at 4° C.

The product is filtered off and washed with 4 liters of water.

The crystalline mass from the two filtrations is resuspended in 50 liters of water and dissolved under hot conditions.

The solution is allowed to crystallise overnight at 4° C.

The product is filtered off and washed with 5 liters of water. The butanedisulphonic acid sodium salt is dried under vacuum.

A further product fraction is obtained by concentrating the mother liquors to 10 liters, and leaving this to crystallise overnight at 4° C., then filtering off the product and drying it under vacuum.

In this manner 25.2 kg of 1,4-butanedisulphonic acid disodium salt monohydrate are obtained (90 moles, 90% molar yield).

The product was identified by elementary analysis and corresponds to the formula $C_4H_8O_6S_2Na_2.H_2O$:

|  | % C | % H | % S |
| --- | --- | --- | --- |
| Calculated | 17.1 | 3.6 | 22.9 |
| Found | 17.1 | 3.7 | 22.9 |

A column was prepared containing 200 liters of Amberlite IR 120 resin previously activated with 6N HCl until the disappearance of the $Na^+$ ion from the eluate, and washed with distilled water until the $Cl^-$ ion disappeared from the eluate.

25.2 kg of 1,4-butanedisulphonic acid disodium salt monohydrate are dissolved in 300 liters of water and fed to the head of the column. The eluate containing the 1,4-butanedisulphonic acid is collected, and the column is washed with water until the pH of the eluate has reached 4.

It is diluted to a final volume of 900 liters to obtain a 0.2N solution of 1,4-butanedisulphonic acid, which is used as such for the preparation of the corresponding SAMe salt.

Operating in an analogous manner but using 20.2 kg of 1,3-dibromopropane as starting material, 900 liters of a 0.2N solution of 1,3-propanedisulphonic acid are obtained.

Using 23 kg of 1,5-dibromopentane, 900 liters of a 0.2N solution of 1,5-pentanedisulphonic acid are obtained.

Using 24.4 kg of 1,5-dibromohexane, 900 liters of a 0.2N solution of 1,6-hexanedisulphonic acid are obtained.

Using 27.2 kg of 1,8-dibromooctane, 900 liters of a 0.2N solution of 1,8-octanedisulphonic acid are obtained.

Finally, using 30 kg of 1,10-dibromodecane, 900 liters of a 0.2N solution of 1,10-decanedisulphonic acid are obtained.

EXAMPLE 2

Preparation of the salt SAMe.1,5 (1,4-butanedisulphonate)

220 liters of ethyl acetate and 220 liters of water are added at ambient temperature to 1800 kg of yeast enriched with SAMe (6.88 g/kg) in accordance with Schlenk [Enzymologia 29, 283 (1965)].

After energetic agitation for 30 minutes, 1000 liters of 0.35N sulphuric acid are added, and agitation is continued for a further 1½ hours.

The mixture is filtered through a rotary filter, which is washed with water to obtain 2800 liters of solution containing 4.40 g/l of SAMe, equal to 99.5% of that present in the starting material.

The SAMe solution obtained in this manner (pH 2.5) is fed to an ultrafiltration plant using tubular membranes with a 10,000 cut-off.

The permeate leaving the membranes is collected in a suitable vessel, whereas the concentrate is continuously recycled to a final volume of 200 liters. At this point, distilled water is added and recycling is continued until the SAMe is completely extracted. 3500 liters of ultrafiltered lysate are obtained, which is adjusted to pH 5 by adding 2N NaOH.

A column is prepared containing 400 liters of Amberlite CG 50 resin in $H^+$ form, which has been carefully washed with distilled water.

The lysate is passed through the resin column at a rate of 800 l/h, kept constant during the entire procedure.

400 liters of distilled water, 3200 liters of 0.1M acetic acid, and 400 liters of distilled water are then passed through in succession.

The SAMe is eluted with 800 liters of 0.2N 1,4-butanedisulphonic acid. The 800 liters of eluate obtained in this manner contain approximately 10 kg of SAMe.

A column is prepared containing 400 liters of Amberlite XAD4 resin which had been previously activated with 800 liters of 0.1N NaOH and 800 liters of 0.1N $H_2SO_4$, and then carefully washed with distilled water.

The previously obtained SAMe solution is passed through the column at a rate of 200 l/h, kept constant during the entire procedure.

400 liters of 20 mN 1,4-butanedisulphonic acid are then passed through.

The eluate containing the SAMe (about 1000 liters contining 10 kg of SAMe) is collected.

The solution obtained in this manner is fed to a reverse osmosis plant of the flat type using polyamide desalination membranes.

In this plant, the SAMe solution is concentrated to 80 liters containing 9.9 kg of SAMe. 5 liters of a 2N solution of butanedisulphonic acid are added.

The solution obtained in this manner is fed to a spray drying plant fed with air at 160° C.

The dry product is continuously extracted from the plant.

18 kg of powdery product are obtained, having the following composition on analysis:
SAMe: 54.9%
1,4-butanedisulphonic acid: 44.9%
$H_2O$: 0.2%
corresponding to the salt SAMe.1,5 (1,4-butanedisulphonate).

The product is in the form of a crystalline white powder soluble in water to 30% by weight with the formation of a colourless solution, and insoluble in common organic solvents.

Using thin layer chromatography in accordance with Anal. Biochem. 4, 16-28 (1971), the product is found to be free from any impurity.

| Elementary analysis: $C_{15}H_{22}N_6O_5S.1,5\ C_4H_{10}O_6S_2$ | | |
|---|---|---|
| % N | % C | % H |
| Calculated 11.6 | 34.7 | 5.1 |
| Found 11.5 | 34.8 | 5.1 |

The ultraviolet spectrum for the product shows an absorption maximum (in buffer of pH 4) at 258.5 nm, with $E_{1\%} = 193$.

EXAMPLE 3

Preparation of the salt SAMe.1,5 (1,3-propanedisulphonate)

The procedure of Example 2 is followed, but using 1,3-propanedisulphonic acid instead of 1,4-butanedisulphonic acid.

17.45 kg of powder are obtained which on analysis shows the following composition:
SAMe; 56.5%
1,3-propanedisulphonic acid 43.3%
$H_2O$: 0.2%
corresponding to the salt SAMe.1,5 (1,3-propanedisulphonate).

The product is in the form of a crystalline white powder soluble in water to 30% by weight with the formation of a colourless solution, and insoluble in common organic solvents.

Thin layer chromatography in accordance with Anal. Biochem. 4, 16-28 (1971) shows that the product is free from any impurity.

| Elementary analysis: $C_{15}H_{22}N_6O_5S.1,5\ C_3H_8O_6S_2$ | | |
|---|---|---|
| % N | % C | % H |
| Calculated 11.9 | 33.2 | 4.8 |
| Found 11.9 | 33.1 | 4.8 |

The ultraviolet spectrum for the product shows an absorption maximum (in buffer of pH 4) at 258.5 nm with $E_{1\%} = 199$.

EXAMPLE 4

Preparation of the salt SAMe.1,5 (1,5-pentanedisulphonate)

The procedure of Example 2 is followed, but 1,5-pentanedisulphonic acid is used in place of the 1,4-butanedisulphonic acid.

18.5 kg of powder are obtained which on analysis shows the following composition:
SAMe 53.3%
1,5-pentanedisulphonic acid: 46.5%
$H_2O$: 0.2%
corresponding to the salt SAMe.1,5 (1,5-pentanedisulphonate).

The product is in the form of a crystalline white powder soluble in water to 30% by weight with the formation of a colourless solution, and insoluble in common organic solvents.

Thin layer chromatography in accordance with Anal. Biochem. 4, 16-28 (1971) shows that the product is free from any impurity.

| Elementary analysis: $C_{15}H_{22}N_6O_5S.1,5\ C_5H_{12}O_6S_2$ | | |
|---|---|---|
| % N | % C | % H |
| Calculated 11.3 | 36.2 | 5.4 |
| Found 11.4 | 36.2 | 5.3 |

The ultraviolet spectrum for the product (in buffer of pH 4) shows an absorption maximum at 258.5 nm with $E_{1\%} = 188$.

EXAMPLE 5

Preparation of the salt SAMe.1,5 (1,6-hexanedisulphonate)

The procedure of Example 2 is followed, but 1,6-hexanedisulphonic acid is used in place of the 1,4-butanedisulphonic acid.

19 kg of powder are obtained which on analysis shows the following composition:
SAMe: 51.8%
1,6-hexanedisulphonic acid: 48%
$H_2O$: 0.2%
corresponding to the salt SAMe.1,5 (1,6-hexanedisulphonate).

The product is in the form of a crystalline white powder soluble in water to 30% by weight with the formation of a colourless solution, and insoluble in common organic solvents.

Thin layer chromatography in accordance with Anal. Biochem. 4, 16-28 (1971) shows that the product is free from any impurity.

| Elementary analysis: $C_{15}H_{22}N_6O_5S.1,5\ C_6H_{14}O_6S_2$ | | |
|---|---|---|
| % N | % C | % H |
| Calculated 10.9 | 37.6 | 5.6 |
| Found 10.8 | 37.5 | 5.6 |

The ultraviolet spectrum for the product (in buffer of pH 4) shows an absorption maximum at 258.5 nm with $E_{1\%} = 182$.

EXAMPLE 6

Preparation of the salt SAMe.1,5 (1,8-octanedisulphonate)

The procedure of Example 2 is followed, but 1,8-octanedisulphonic acid is used in place of the 1,4-butanedisulphonic acid. 20 kg of powder are obtained, which on analysis shows the following composition:
SAMe 49.3%
1,8-octanedisulphonic acid: 50.5%
$H_2O$: 0.2%
corresponding to the salt SAMe.1,5 (1,8-octanedisulphonate).

The product is in the form of a crystalline white powder soluble in water to 30% with the formation of a colourless solution, and insoluble in common organic solvents.

Thin layer chromatography in accordance with Anal. Biochem. 4, 16–28 (1971) shows that the product is free from any impurity.

Elementary analysis:
$C_{15}H_{22}N_6O_5S.1,5\ C_8H_{18}O_6S_2$

|  | % N | % C | % H |
|---|---|---|---|
| Calculated | 10.4 | 40.0 | 6.0 |
| Found | 10.4 | 39.9 | 5.9 |

The ultraviolet spectrum for the product (in buffer of pH 4) shows an absorption maximum at 258.5 nm with $E_{1\%} = 173$.

EXAMPLE 7

Preparation of the salt SAMe.1,5 (1,10-decanedisulphonate)

The procedure of Example 2 is followed, but 1,10-decanedisulphonic acid is used in place of the 1,4-butanedisulphonic acid.

21 kg of powder are obtained which on analysis shows the following composition:
SAMe: 46.8%
1,10-decanedisulphonic acid: 53%
$H_2O$: 0.2%
corresponding to the salt SAMe.1,5 (1,10-decanedisulphonate).

The product is in the form of a crystalline white powder soluble in water to 20% by weight with the formation of a colourless solution, and insoluble in common organic solvents.

Thin layer chromatography in accordance with Anal. Biochem. 4, 16–28 (1971) shows that the product is free from any impurity.

Elementary analysis:
$C_{15}H_{22}N_6O_5S.1,5\ C_{10}H_{22}O_6S_2$

|  | % N | % C | % H |
|---|---|---|---|
| Calculated | 9.8 | 42.3 | 6.5 |
| Found | 9.9 | 42.4 | 6.5 |

The ultraviolet spectrum for the product (in buffer of pH 4) shows an absorption maximum at 258.5 nm with $E_{1\%} = 164$.

EXAMPLE 8

Injectable pharmaceutical compositions containing S-adenosyl-L-methionine salts of disulphonic acids, with lysine as the buffer agent.

| | | |
|---|---|---|
| a) | a lyophilised vial contains: | |
| | SAMe.1,5 (1,4-butanedisulphonate) equivalent to SAMe ion | 364 mg 200 mg |
| | a solvent vial contains: | |
| | Lysine base | 150 mg |
| | Water for injectable solutions quantity to make up to | 3 ml |
| b) | a lyophilised vial contains: | |
| | SAMe.1,5 (1,4-butanedisulphonate) equivalent to SAMe ion | 729 mg 400 mg |
| | a solvent vial contains: | |
| | Lysine base | 300 mg |
| | Water for injectable solutions quantity to make up to | 5 ml |
| c) | a lyophilised vial contains: | |
| | SAMe.1,5 (1,4-butanedisulphonate) equivalent to SAMe ion | 1821 mg 1000 mg |
| | a solvent vial contains: | |
| | Lysine base | 750 mg |
| | Water for injectable solutions quantity to make up to | 10 ml |

I claim:

1. A process for producing stable sulphoadenosyl-L-methionine (SAMe) salts corresponding to the formula:

$$SAMe.n(CH_2)_m(SO_3H)_2$$

where n can vary from 1 to 2 and m can vary from 3 to 12, comprising:
 a) enriching a starting yeast with SAMe by adding methionine to cultures of microorganisms selected from the group consisting of *Saccharomyces cerevisiae* and *Candida utilis*;
 b) lysing the cells and recovering by filtration a cell lysate as a solution rich in SAMe;
 c) prepurifying the cell lysate by ultrafiltration;
 d) passing the prepurified cell lysate through a column of weak acid ion exchange resin and eluting the column with a disulphonic acid of formula $(CH_2)_m(SO_3H)_2$ wherein m is 3 to 12;
 e) passing the eluate of said column thorough a column of absorption resin and washing said column of absorption resin with a disulphonic acid of formula $(CH_2)_m(SO_3H)_2$ wherein m is 3 to 12 and recovering the eluate thereof;
 f) concentrating the eluate from the column of absorption resin by means of reverse osmosis; and
 g) drying the concentrated eluate of step f).

2. A process for producing stable SAMe salts as claimed in claim 1, in which stage b) is effected by treating the enriched yeast firstly with a solution of water and ethyl acetate and then with a disulphonic acid of between 0.1N and 0.5N.

3. A process for producing stable SAMe salts as claimed in claim 1, in which stage c) is effected by subjecting the cell lysate to ultrafiltration, using membranes with a nominal 4. A process for producing stable SAMe salts as claimed in claim 1, in which stage d) is effected by passing the prepurified lysate through a column of weak acid resin ion exchange in $H^+$ form at a pH of between 3.5 and 7.

5. A process for producing stable SAMe salts as claimed in claim 1, in which stage d) is effected by passing said prepurified lysate through said column at a rate of between 1 and 3 liquid volumes/hour per resin volume.

6. A process for producing stable SAMe salts as claimed in claim 1, in which stage d) is effected by passing said prepurified lysate through said column containing a resin quantity of between 10 and 50 liters per kg of SAMe.

7. A process for producing stable SAMe salts as claimed in claim 1, wherein the column of the weak acid ion exchange resin is eluted with an 0.2N disulphonic acid solution.

8. A process for producing stable SAMe salts as claimed in claim 1, in which stage e) is effected by passing the eluate of stage d) through a column of absorption resin comprising an absorption polymer selected from the group consisting of polystyrene and acrylic ester at a rate of between 0.2 and 1 liquid volume/hour per resin volume.

9. A process for producing stable SAMe salts as claimed in claim 1, wherein stage f) is effected by reverse osmosis using desalination membranes of high NaCl rejection.

10. A process for producing stable SAMe salts as claimed in claim 1, in which stage g) is effected by drying the concentrated eluate of step f) by atomisation in a chamber fed with hot air.

11. A process for producing stable SAMe salts as claimed in claim 1, wherein said hot air is fed to said chamber at a temperature of between 140° and 200° C. and leaves said chamber at a temperature of between 40° and 100° C.

12. A process for producing stable SAMe salts as claimed in claim 10, wherein said solution is fed to said chamber at an SAMe concentration of between 100 and 200 g/l.

13. A process for producing stable SAMe salts as claimed in claim 1 which includes passing the disulphonic acid eluate of said column of weak acid exchange resin through said column of absorption resin until the SAMe disappears from the eluate of said column of weak acid exchange resin and then washing said column of absorption resin of stage e) with said disulphonic acid.

* * * * *